US005728055A

United States Patent [19]
Sebastian

[11] Patent Number: 5,728,055
[45] Date of Patent: Mar. 17, 1998

[54] THERAPEUTIC LUMBOSACRAL APPLIANCE

[75] Inventor: Thomas Vincent Sebastian, Reading, Pa.

[73] Assignee: Fisher Scientific Company, Pittsburgh, Pa.

[21] Appl. No.: 593,812

[22] Filed: Jan. 30, 1996

[51] Int. Cl.$^6$ .................................................. A61F 5/00
[52] U.S. Cl. ............................ 602/19; 602/13; 2/44; 2/311; 128/96.1; 128/100.1
[58] Field of Search ....................... 602/18, 19, 13; 128/96.1, 100.1, 101.1; 2/312, 311

[56] References Cited

U.S. PATENT DOCUMENTS

| | | | |
|---|---|---|---|
| 4,703,750 | 11/1987 | Sebastian et al. | 602/19 |
| 4,993,409 | 2/1991 | Grim | 602/19 |
| 5,399,150 | 3/1995 | Saunders | 602/19 |

Primary Examiner—Richard J. Apley
Assistant Examiner—Kim M. Lee
Attorney, Agent, or Firm—Wenderoth, Lind & Ponack

[57] ABSTRACT

A therapeutic appliance is provided for application to the lumbar spine so as to overly the sacrum and sacroiliac joints. The therapeutic appliance is formed basically by an air bladder having a plurality of air chambers. The air chambers include a central air chamber elongated in a direction transverse to a longitudinal direction of the air bladder, and inclined air chambers provided on opposing sides of the transverse air chamber and elongated in directions inclined relative to the transverse air chamber downwardly and toward the respective longitudinal ends of air bladder. Gap air chambers are also provided in the gaps formed between the transverse air chamber and the innermost inclined air chambers. Longitudinally extending air chambers are provided at opposing longitudinal ends of the air bladder. The arrangement of the air chambers in the air bladder is such that, when the air chambers are inflated, the air bladder is contracted by forces acting in a direction downwardly and inwardly toward the longitudinal midline of the air bladder. The air bladder can be secured to a wearer's body by providing the air bladder in the form of a belt, or by attaching the air bladder to a pair of pants or a torso shell. When positioned properly on the wearer's body, the inwardly and downwardly inclined contraction forces help to prevent the air bladder from riding up along the wearer's body which would otherwise be the tendency.

21 Claims, 4 Drawing Sheets

THERAPEUTIC LUMBOSACRAL APPLIANCE

FIELD OF THE INVENTION

The present invention relates generally to a lumbosacral (or sacrolumbar) therapeutic appliance and, more specifically, to a lumbosacral therapeutic appliance which utilizes inflatable air chambers arranged to relieve pain in the areas of the lumbosacral spine and sacroiliac joints by maintaining normal alignment of the osseous structures and providing static stretch to paravertebral muscles to alleviate unwanted muscles spasms and fatigue.

BACKGROUND OF THE INVENTION

Lower back pain is a common problem and is often the result of mechanical and physiologic derangement of the osseous, ligamentous and muscular structures of the lower back region. For purposes of the following discussion, the terms lower back and lower back region refer to the region of the lumbar and sacral portions of the spinal column and the sacroiliac joints. The proper inter-relationships between the osseous, ligamentous and muscular structures in this lower back region are of extreme importance, because these structures are responsible for a large amount of the weight bearing and structural support required in lifting, exercising and many other common activities.

Traumatic and chronic injuries to any one or more of the osseous, ligamentous and muscular structures in the lower back region often result in dysfunction and subsequent pain and, possibly, in further strain and injury to the other of these structures. Similarly, injury at one level of the spine will often adversely affect adjacent structures, thereby leading to dysfunction in areas relatively distant from the original site of the injury or abnormality. The maintenance of proper posture is essential in preventing such injuries and to attaining optimal functioning. Proper posture is the result of correct vertebral alignment, balanced ligamentous support and limitation of excessive or unwanted movement, as well as flexibly balanced and strong musculature regulating and stabilizing motion.

While these objectives may be met by a variety of therapeutic modalities, lower back braces used for this purpose should have certain characteristics including: (1) contour fitting of the normal spinal/pelvic curvatures; (2) sufficient firmness to prevent buckling or unwanted binding of the appliance during wearer movement; (3) adequate flexibility to allow free and unrestricted normal ranges of motions; (4) adequate coverage of anatomically and functionally related segments of the spine with therapeutic forces sufficient for maximum effectiveness; (5) contour shaping of the pelvic segment to avoid unwanted bony bridging effect of the iliac crests which inhibits desired counter-pressure over midline and adjacent paravertebral muscles and osseous elements; and (6) sufficient general comfort, lack of bulkiness, and ease of use. Prior art therapeutic appliances, including therapeutic air-inflated appliances, failed in attaining one or more of these therapeutic characteristics.

Particular reference is made to a therapeutic lumbosacral appliance disclosed in U.S. Pat. No. 4,703,750 and depicted in FIG. 11. This appliance, which is designed as a belt-type appliance, relies on inflatable air chambers 102–105 to provide the necessary support and form-fitting to relieve pain in the lumbosacral and sacroiliac regions by maintaining normal alignment of the osseous structures and providing static stretch to the paravertebral muscles to alleviate unwanted muscle spasms and fatigue. Non-air filled portions 101 are provided at the sides of the appliance, and an air conduit 106 is provided for inflating and deflating the air chambers. The air chambers of this prior art appliance 100 include a central air chamber which overlies the midline of the lumbar spine and extends down to the sacrum, and transversely extending chambers which follow the contours of the iliac crests. Longitudinally extending air chambers 104 and arcuate air chambers 104a are also provided to overly the sacrum and lie between the sacroiliac joints as well as just beneath the posterior superior iliac spines. The longitudinal and arcuate air chambers 104, 104a function to anchor and prevent the tendency of the appliance 100 to move upwardly on the wearer's body.

Figure 11:
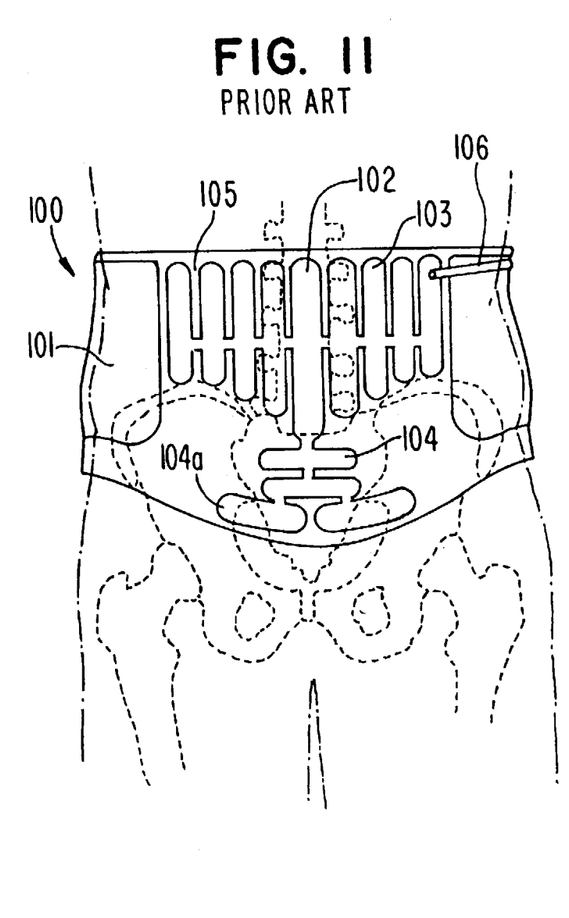
FIG. 11 shows a prior art therapeutic appliance in a use position on a human body.

However, this prior art appliance 100 is rather bulky, especially in the height direction, due to the provision of the longitudinal and arcuate air chambers 104, 104a, and is therefore less comfortable to wear and more difficult to arrange when taking into account, for example, clothing worn beneath the appliance.

SUMMARY OF THE INVENTION

A general object of the present invention is to provide a lumbosacral therapeutic appliance having all of the above-discussed desirable characteristics, and to therefore obviate the disadvantages of the prior art therapeutic appliances.

A more specific object of the present invention is to provide a lumbosacral therapeutic appliance which does not move upwardly (or ride up) on the wearer's body, yet is free from bulkiness and therefore easy to use and comfortable to wear.

In particular, the present invention provides an improved lumbosacral therapeutic appliance which utilizes inflatable air chambers designed to relieve pain in the lumbosacral and sacroiliac region by maintaining normal alignment of the osseous structures and providing static stretch to paravertebral muscles to alleviate unwanted muscle spasms and fatigue. The therapeutic appliance of the present invention performs these functions without unduly limiting the normal motions of the wearer. Furthermore, the device is relatively compact and non-bulky, and is therefore of optimum comfort to the wearer. Likewise, the appliance is easy to apply and wear.

An additional object of the present invention is to provide such therapeutic appliance in belt form, or in a form to be applied to the human body by other means such as by attachment to pants or other clothing or by attachment to another structure such as a semi-rigid shell which is, in turn, applied to the subject region of the body.

According to the invention, the therapeutic appliance of the present invention is to be applied to the lumbosacral region of the human body to overly the sacrum and sacroiliac joints. The appliance includes an air bladder elongated along a longitudinal direction and having first and second longitudinal ends, the air bladder having a length in the longitudinal direction sufficient to wrap at least partly around the human body while overlying the sacrum and sacroiliac joints, and the air bladder comprising a plurality of air chambers located between the first and second longitudinal ends. At least one air supply passage is coupled with at least one of the air chambers and is in fluid communication with the plurality of the air chambers. Among the air chambers are a plurality of first inclined air chambers disposed longitudinally between the first longitudinal end of the air bladder and a transversely extending longitudinal midline of the air bladder, and a plurality of second inclined air chambers disposed longitudinally between the second longitudinal end of the air bladder and the longitudinal midline. Each of the first inclined air chambers is elongated in a direction inclined relative to the longitudinal midline, such that the longitudinal midline forms a downwardly opening acute angle with a central longitudinal line of each of the first inclined chambers. Similarly, each of the second inclined air chambers is elongated in a direction inclined relative to the longitudinal midline, such that the longitudinal midline forms a downwardly opening acute angle with a central longitudinal line of each of the second inclined chambers.

In addition, the air chambers include a centrally located transverse air chamber elongated along the transversely extending longitudinal midline, such that the midline is coincident with a central longitudinal line of the transverse air chamber.

The central longitudinal lines of the first inclined air chambers are inclined downwardly and outwardly from the central longitudinal line of the transverse air chamber in a direction toward the first longitudinal end of the air bladder. The central longitudinal lines of the second inclined air chambers are inclined downwardly and outwardly from the from the central longitudinal line of the transverse air chamber in a direction toward the second longitudinal end of the air bladder. Thus, a first gap is formed between the transverse air chamber and an innermost one of the first inclined air chambers, and such first gap is greater adjacent a bottom end of the transverse air chamber than adjacent a top end thereof. Similarly, a second gap is formed between the transverse air chamber and an innermost one of the second inclined air chambers and the second gap is greater adjacent the bottom end of the transverse air chamber than adjacent the top end thereof. First and second gap air chambers, which are preferably generally triangular in shape, are disposed in the lower ends of the first and second gaps, respectively.

Also preferably, the central longitudinal lines of the first inclined air chambers are mutually parallel, and the central longitudinal lines of the second inclined air chambers are mutually parallel. The first inclined air chambers are progressively shorter in length in a direction away from the transverse air chamber toward the first longitudinal end of the air bladder, and the second inclined air chambers are progressively shorter in length in a direction away from the transverse air chamber toward the second longitudinal end of the air bladder. First and second pluralities of longitudinal air chambers are provided adjacent the first and second longitudinal ends of the air bladder.

The air chambers are designed and arranged in such a manner as to define a means for causing contraction of the air bladder in directions downwardly and inwardly toward the longitudinal midline, upon inflation of the air chambers. This function acts to prevent the air bladder from riding upwardly on the wearer's body.

Preferably, the air bladder is formed by first and second layers of a material having sufficiently low stretchability and sufficient form-retaining characteristics to allow accurate reproduction of an inflated configuration of the air chambers, the air chambers being separated by joints between the first and second layers. The air bladder can be secured to the human body by the provision of elongated belt ends secured to the first and second longitudinal ends of the bladder, by attaching the air bladder to pants, or by attaching the air bladder to a semi-rigid shell attached at least partly about the human body.

BRIEF DESCRIPTION OF THE DRAWINGS

The objects, advantages and details of the present invention will be more fully understood from the following detailed description of the invention with reference to the accompanying drawings, in which.

DETAILED DESCRIPTION OF THE INVENTION

A therapeutic appliance according to the present invention will now be described in detail with reference to FIGS. 1–10. Like parts are denoted by like reference characters throughout the drawing figures.

Figure 3:
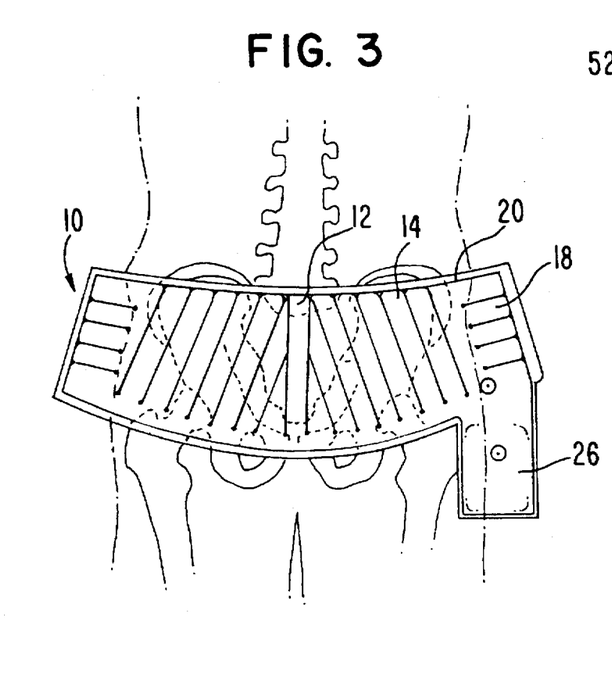
FIG. 3 shows the therapeutic appliance of the present invention superposed over the lumbosacral region of a human body.
Figure 10:
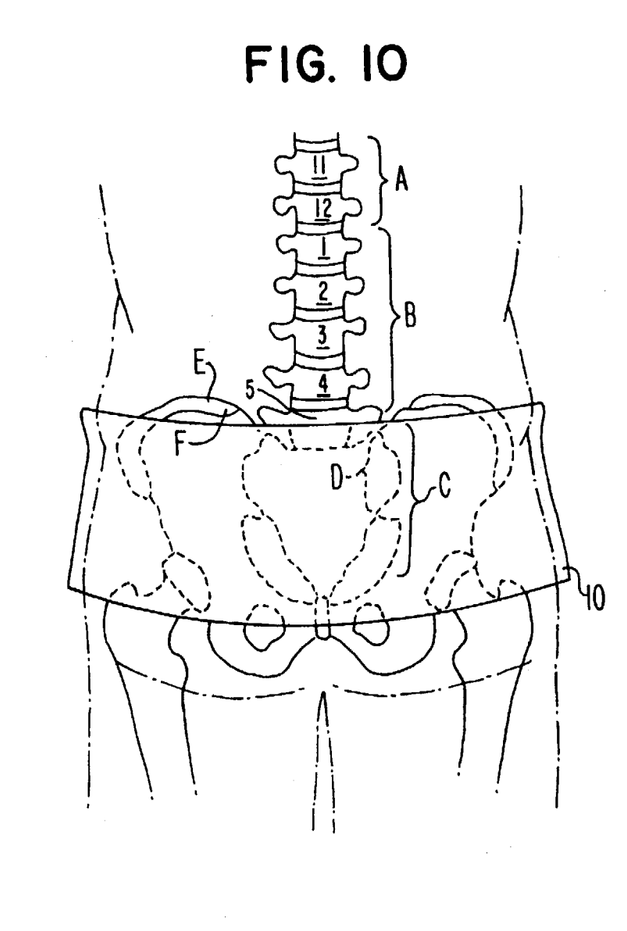
FIG. 10 schematically depicts the use position of the therapeutic appliance of the present invention over the lumbosacral region of the human body.

The basic form of the therapeutic appliance of the present invention is that of an air bladder 10 formed with discrete inflatable air chambers 12–18. FIGS. 3 and 10 illustrate the anatomical regions of the human body over which the air bladder 10 of the present invention is to be superposed when properly worn. Referring especially to FIG. 10, the lumbar spine (B) consists of five vertebrae in normal subjects, and each adjacent pair of the vertebrae is separated by an intervening intervertebral disc. The sacrum (C) consists of five anatomically fused segments. The sacroiliac joints (D) represent articulation points of the sacrum and iliac bones on either side of the midline (which runs along the spinal column). The iliac crest (E) is that portion of the iliac bone lying highest and ending in the posterior superior iliac spine (F) which is the most posterior bony protuberance. Both the iliac crests (E) and the posterior superior iliac spines (F) tend to hold prior art therapeutic appliances away from the spine and the paravertebral musculature which the appliance is intended to treat, thereby diminishing the intended therapeutic counter-pressure.

Figure 1:
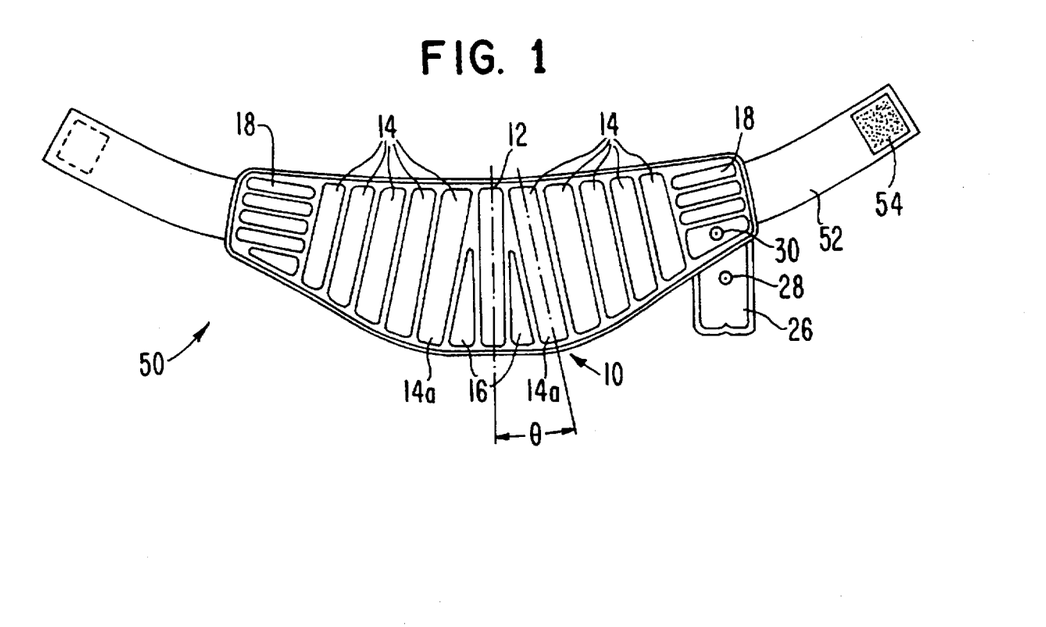
FIG. 1 shows a therapeutic appliance according to the present invention embodied in the form of a therapeutic belt.
Figure 2:
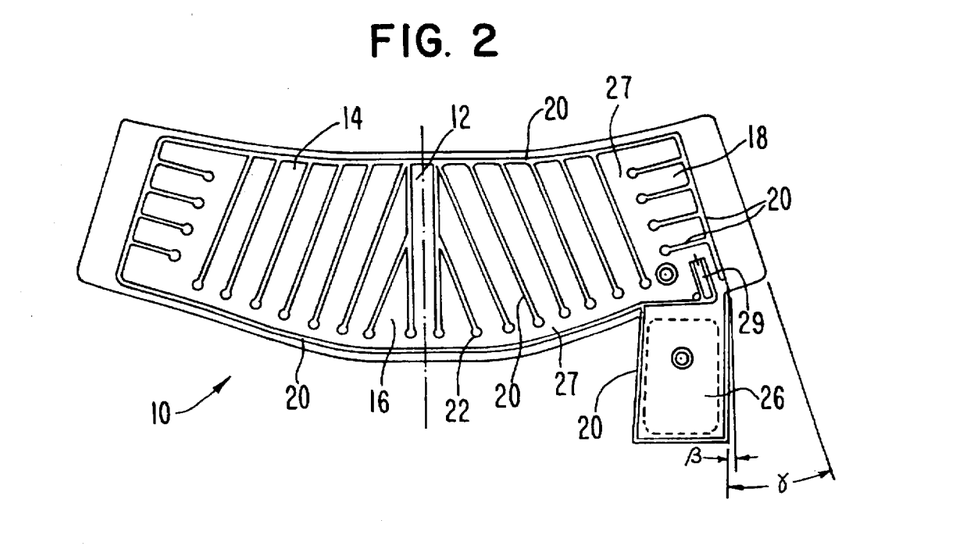
FIG. 2 is a schematic view of a basic form of the therapeutic appliance of the present invention.

With reference to FIGS. 1–5 and, in particular, FIGS. 1 and 2, the air bladder 10 of the therapeutic appliance of the present invention is preferably shaped as shown in FIGS. 1 and 2 so as to have an upper edge which is slightly upwardly concave, and a lower edge which is upwardly concave to a greater degree than the upper edge.

The air chambers 12–18 formed in the air bladder 10 include a central transverse air chamber 12 elongated in a direction transverse to a longitudinal direction of the air bladder 10. The central transverse air chamber 12 lies along the longitudinal midline of the air bladder 10. Inclined air chambers 14 are formed on either side of the central transverse air chamber 12. The inclined air chambers 14 located on the left side of the central transverse air chamber 12 as shown in FIGS. 1 and 2 are referred to as first inclined air chambers 14 and are elongated in a direction inclined relative to the central transverse air chamber 12. In other words, central longitudinal lines of each of the first inclined air chambers 14 located on the left side of the transverse air chamber 12 are inclined relative to the central longitudinal line of the transverse air chamber 12 in a direction downwardly and outwardly toward the first longitudinal end (left end in FIGS. 1 and 2) of the air bladder 10, such that an acute angle θ is formed between the central longitudinal line of the transverse air chamber 12 and the central longitudinal line of each of the first inclined air chambers 14 located to the left of the air chamber 12.

The inclined air chambers 14 located on the right side of the transverse air chamber 12 as shown in FIGS. 1 and 2 are referred to as second inclined air chambers and are elongated in an inclined direction relative to the central transverse air chamber 12, but these second inclined air chambers 14 located to the right of the air chamber 12 are inclined downwardly and toward the second longitudinal end (right end in FIGS. 1 and 2) of the air bladder 10. In the preferred form of the invention, the acute angles θ between the central longitudinal line of the transverse air chamber 12 and the central longitudinal lines of the inclined air chambers 14 are in the range of approximately 7° to 16° and preferably about 11°.

Because of the inclination of the air chambers 14 relative to the air chamber 12, gaps are formed between the air chamber 12 and the innermost inclined air chambers 14a, wherein the gaps are greater adjacent the bottom end of the air chambers than adjacent the top ends thereof. First and second gap air chambers 16 are provided in the gaps formed between the transverse air chamber 12 and the respective innermost inclined air chamber 14a, in order to ensure that proper contraction of the air bladder occurs upon inflation of the air bladder. In order to correctly fill the gaps and enable suitable contraction of the air bladder 10, the gap air chambers 16 are triangular in the preferred form of the invention.

In particular, due to the arrangement of the air chambers 12–16 of the air bladder 10, the air bladder will contract in directions inclined inwardly and downwardly from the first and second longitudinal ends of the air bladder 10, respectively. This contraction of the air bladder 10 upon inflation of the air chambers is an essential feature of the present invention in that it allows the air bladder to be comfortably worn in its correct therapeutic location on the human body without having the air bladder ride upwardly out of its correct location, which would otherwise be the normal tendency of the air bladder. In other words, the inflation of the air chambers causes contraction of the air bladder 10 in directions inwardly and downwardly from the longitudinal ends of the air bladder 10 so as to create inwardly and downwardly directed forces to prevent the air bladder 10 from riding upwardly on the wearer's body and to thereby maintain the air bladder 10 in its correct therapeutic location.

Longitudinally elongated air chambers 18 are also provided adjacent the first and second longitudinal ends of the air bladder 10. These air chambers 18, when inflated, will cause the longitudinal ends of the air bladder to contour to the curvature of the sides of the wearer's body to further aid in the holding of the air bladder 10 in the proper therapeutic position.

As illustrated in FIGS. 1 and 2, the air bladder is provided with a pump 26 for introducing air into the air bladder to inflate the individual air chambers 12–18. As can be seen best in FIG. 2, the air chambers are all fluidically interconnected and fluidically connected with the air discharge port 29 of the pump 26 by air passages 27. The air pump 26 can be any suitable pump effective to discharge air into the air bladder 10 while preventing the air from escaping from the air bladder 10. The pump can be in the form of a simple bulb-type pump with a check valve to prevent back flow of air (as exemplified in FIG. 8), but is preferably a palm-grip pump of the type disclosed in U.S. Pat. No. 5,144,708, the disclosure of which is hereby incorporated by reference. The pump 26 includes an air intake 28, and a pressure relief valve 30 is provided in the air bladder to allow for release of the air pressure in the air chambers to thereby deflate the air bladder 10.

Although the air bladder can be formed in any suitable manner and of any suitable material, it is preferably formed of two polyurethane-coated nylon sheets 10a, 10b (see FIG. 5) having the polyurethane coated sides of the sheets confronting one another and fused together along seal lines 20. Alternatively, the material of the air bladder 10 can be plastic, Nylon or another plastic/Nylon combination. It is also possible that the air bladder 10 can be formed as a unitary molded form rather than from two sheets. The seal lines are located in such a manner as to define the individual air chambers 12–18, and to fluidically intercommunicate all of the air chambers 12–18 via the air passages 27 with the discharge outlet 29 of the pump 26 and with each other. In a preferred form of the invention, each terminal end of a seal line 20 is provided with an enlarged seal portion constituting a strengthening seal portion 22. Also in a preferred form of the present invention, the palm-grip pump 26 is integrally molded with the air bladder 10 upon molding of the air bladder 10. Preferably, the downwardly protruding pump portion 26 is, as shown in FIGS. 1 and 2, slightly inclined relative to a line parallel to the central longitudinal line of the central transverse air chamber 12, by an angle β of about one to five degrees and more preferably about two degrees, in a direction inwardly toward the center of the air bladder 10, in order to improve the ease with which the palm-grip pump 26 can be grasped and pumped with the wearer's hand. As an additional point of reference, the pump portion 26 is inclined relative to a longitudinal end of the air bladder 10 by an angle 7 of about 12 to 20 degrees and more preferably about 16 degrees.

Another important feature of the present invention is that the material of which the air bladder is formed must have sufficient form-retaining capability and low stretchability that the air chambers can be repeatedly inflated and deflated yet retain their desired configurations over a large number of cycles of inflation and deflation. The material must also be of sufficiently low stretchability to provide for the contraction of the air bladder 10 in the desired direction upon inflation of the air chambers.

The air bladder 10 can be mounted to the lumbosacral region of the human body by any suitable means, so long as the air bladder is properly positioned. The contraction forces which occur in the inward and downward direction upon inflation of the air chambers 12–18 will facilitate the maintenance of the correct positioning of the air bladder 10. The longitudinal air chambers 18 which contour to the sides of the wearer's body will also help to maintain the air bladder in its proper therapeutic location.

Figure 4:
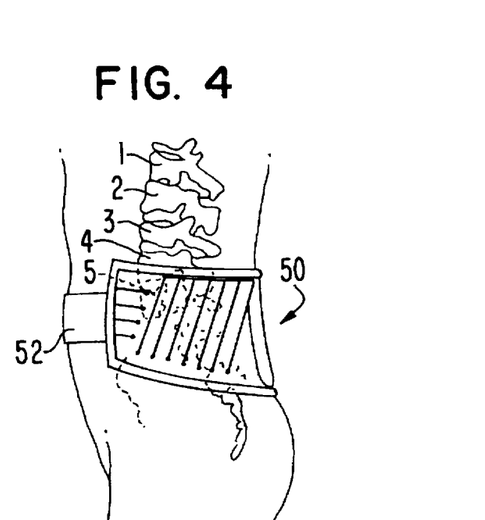
FIG. 4 shows the belt form of the therapeutic appliance of the present invention in a use condition on a human body.
Figure 5:
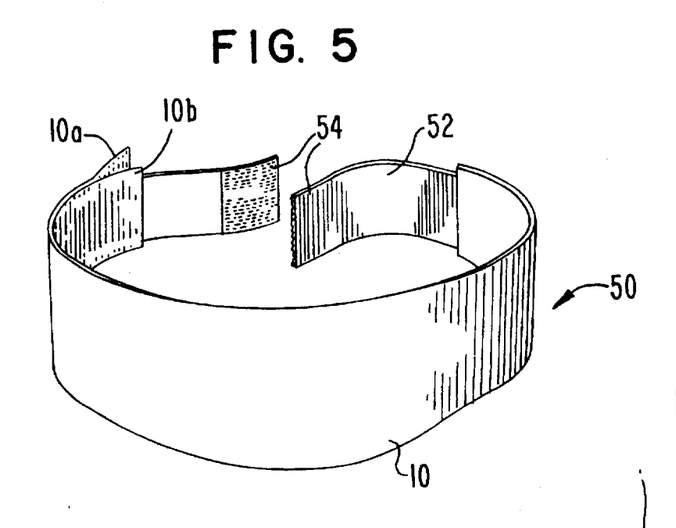
FIG. 5 is a perspective view showing the general shape of the therapeutic appliance embodied in a belt form.

In one form of the present invention, the air bladder 10 is provided in the form of a belt by the provision of belt ends 52. These belt ends can be formed of any suitable material but, in the preferred form of the invention, are formed of neoprene. Velcro members 54 are provided at the ends of the belt ends 52 to enable the belt appliance 50 to be secured to a wearer's body as depicted in FIG. 4. The belt ends 52 can be formed integrally with the air bladder 10 or attached thereto in any suitable manner. However, in the preferred form of the belt appliance 50, each of the belt ends 52 is attached to the air bladder 10 by disposing it between the two sheets 10a, 10b forming the air bladder 10 at a position longitudinally outwardly of the outermost seal line 20. The two layers 10a, 10b at the end of the air bladder are then secured together with the inner end of the belt end 52 therebetween by sewing or the like. It is also possible that the belt ends 52 can be removably attached to the first and second longitudinal ends of the air bladder 10 by suitable means such as, for example, Velcro, snaps, zippers or other attachment elements.

Figure 6:
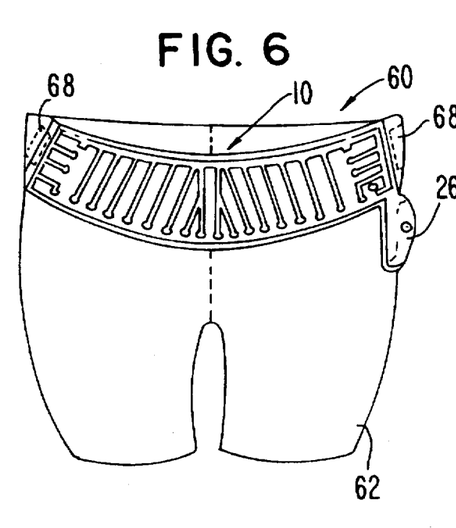
FIG. 6 is a rear view of therapeutic pants with the therapeutic appliance of the present invention attached thereto.
Figure 7:
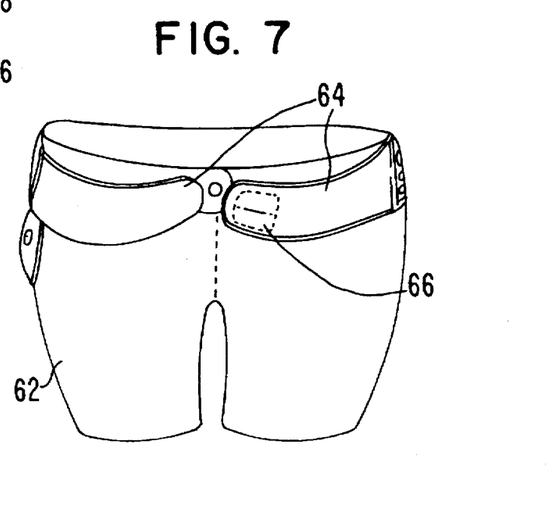
FIG. 7 shows a front view of the therapeutic pants shown in FIG. 6.

FIGS. 6 and 7 show a therapeutic pants appliance 60 wherein an air bladder 10 is secured to a pair of pants 62 which are preferably in the form of exercise shorts formed of, for example, Lycra Spandex. The air bladder 10 is secured preferably to the outside of the pants 62 at the rear side thereof. The attachment of the air bladder to the pants 62 is preferably by means of mutually engageable Velcro elements provided at least at the longitudinal ends of the air bladder 10 and at suitable corresponding locations on the outside of the pants 62. It is also contemplated that the air bladder can be secured to the pants 62 by providing an air bladder pocket near the top of the rear side of the pants 62 into which the air bladder 10 is removably inserted. It is further possible that the air bladder 10 can be non-removably attached to the pants 62 by sewing, insertion into a closed pocket or otherwise. As shown in FIG. 7, the pants 62 are preferably provided with belt portions 64 having Velcro closures 66. In the preferred form of this embodiment of the invention, the belt portions 64 are attached to the pants, not the air bladder. However, it is also contemplated that the belt portions 64 can be secured to the longitudinal ends of the air bladder 10.

Figure 8:
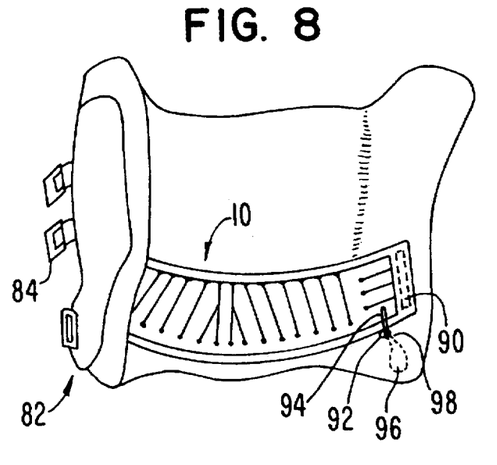
FIG. 8 shows a rear portion of a therapeutic shell appliance utilizing the therapeutic appliance of the present invention.
Figure 9:
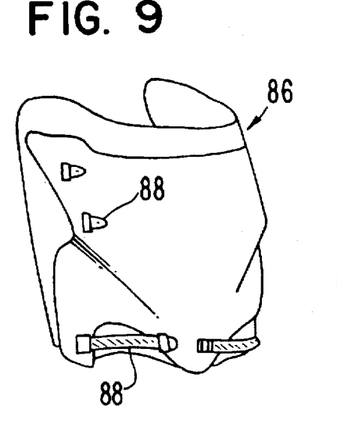
FIG. 9 shows a front portion of the shell appliance shown in FIG. 8.

Another means by which the air bladder 10 can be secured partly about the wearer's body is by securing the air bladder 10 to a torso shell, and then securing the torso shell about the torso and lumbosacral regions of the wearer's body. As shown in FIGS. 8 and 9, the torso shell preferably includes a rear shell 82 configured to conform to the rear and sides of the wearer's body, and a front shell 86 configured to conform to the front and sides of the wearer's body. The front and rear shells 82, 86 can be secured together and about the wearer's body by means of buckle straps 84, 88 provided on the rear and front shells 82, 86, respectively. Of course, the torso shell 82, 86 can be secured about the wearer's body by other suitable means, such as Velcro, snaps, zippers or other attachment elements. The air bladder 10, as shown in FIG. 8, is preferably removably attached to the inside of the rear shell 82 by Velcro elements 90 provided at the longitudinal ends of the air bladder 10 and in suitable corresponding locations inside the rear shell 82. Of course, other means can be provided for removably securing the air bladder to the torso shell, and it is possible that the air bladder 10 can be non-removably secured to the torso shell.

In a preferred form of this embodiment of the invention, the pump for inflating the air bladder 10 is a bulb-type pump 96 provided with a one-way valve to ensure that the air discharged into the air bladder 10 does not backflow. An air tube 94 is attached into the air bladder 10 in fluid communication with the air chambers 12-18, and the air pump bulb 96 is connected to the air tube 94 by a suitable connection joint 98. The air tube 94 extends through an air tube hole 92 formed in the rear shell 82. With this arrangement, the wearer of the therapeutic appliance shown in FIGS. 8 and 9 can access the air pump bulb 96 from the outside of the torso shell.

Upon application of the air bladder 10 to the lumbosacral region of a human body by any of the means disclosed herein or other suitable means, and then upon inflation of the air chambers 12-18, the individual air chambers will cause counter-pressure against strategic therapeutic points in the lumbosacral region. This will help relieve pain normally associated with lifting or other physical acts in the lumbosacral region by, for example, preventing muscle spasms or other commonly occurring dysfunctions. The counter-pressure provided by the inflation of the air chambers 12-18 will also serve as a reminder to the wearer to maintain proper posture during the particular physical activity in question. A particularly important feature of the air chambers in providing the counter-pressure is that the counter-pressure is contoured to aid in maintaining the normal lordotic curvature of the individual wearer's spine as depicted in FIG. 4.

It is further contemplated that the air bladder 10 can be applied to the human body by means of a body cast, a partial body cast, a wet suit, football pads or other sporting equipment or other tight-fitting clothing such as a shirt or jacket.

Although specific preferred embodiments of the present invention have been described above, such description, and the accompanying drawing figures, are for illustrative purposes only. It is to be understood that other embodiments of the present invention will be apparent to those skilled in the art and are intended to be encompassed by the present invention which is defined by the appended claims.

What is claimed is:

1. A therapeutic appliance for application to the sacrolumbar region of the human body to overlie the sacrum and sacroiliac joints, said appliance comprising:

an air bladder elongated along a longitudinal direction and having first and second longitudinal ends and top and bottom edges extending between said first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said first inclined air chambers has a top end adjacent said top edge of said air bladder, and a bottom end adjacent said bottom edge of said air bladder;

wherein each of said first inclined air chambers is inclined in said second direction over an entire length thereof from said top end to said bottom end;

wherein each of said second inclined air chambers is elongated in a third direction inclined relative to said first direction such that said longitudinal midline forms a downwardly opening acute angle with a central longitudinal line of each of said second inclined air chambers;

wherein each of said second inclined air chambers has a top end adjacent said top edge of said air bladder, and a bottom end adjacent said bottom edge of said air bladder; and wherein each of said second inclined air chambers is inclined in said third direction over an entire length thereof from said top end to said bottom end.

2. A therapeutic appliance as recited in claim 1, wherein said central longitudinal lines of said first inclined air chambers are mutually parallel; and said central longitudinal lines of said second inclined air chambers are mutually parallel.

3. A therapeutic appliance as recited in claim 1, wherein a central longitudinal line of said air bladder is an upwardly concave curved line.

4. A therapeutic appliance as recited in claim 1, wherein said air bladder comprises first and second layers of a material having sufficient form-retaining capability to allow accurate reproduction of an inflated configuration of said air chambers, said air chambers being separated by joints between said first and second layers.

5. A therapeutic appliance as recited in claim 1, further comprising
means for mounting said air bladder to the human body so as to overlie the sacrum and sacroiliac joints.

6. A therapeutic appliance as recited in claim 1, further comprising
elongated belt ends respectively secured to said first and second longitudinal ends of said bladder, mutually engageable closure elements being respectively provided on said elongated belt ends, whereby said air bladder and said belt ends together constitute a therapeutic belt.

7. A therapeutic appliance as recited in claim 1, further comprising
pants; and
means for securing said air bladder to said pants such that, when said pants are worn on the human body, said air bladder is positioned to overlie the sacrum and sacroiliac joints.

8. A therapeutic appliance for application to the sacrolumbar region of the human body to overlie the sacrum and sacroiliac joints, said appliance comprising:
an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;
at least one air supply passage coupled with at least one of said air chambers and in fluid communication with said plurality of said air chambers;
an air pump fluidically connected to said at least one air supply passage; and
wherein said air pump is attached to said air bladder adjacent one of said first and second longitudinal ends of said air bladder and projects downwardly therefrom in a direction inclined longitudinally inwardly toward said longitudinal midline of said air bladder.

9. A therapeutic appliance as recited in claim 8, wherein said air pump is integrally molded with said air bladder.

10. A therapeutic appliance for application to the sacrolumbar region of the human body to overlie the sacrum and sacroiliac joints, said appliance comprising:
an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;
at least one air supply passage coupled with at least one of said air chambers and in fluid communication with said plurality of said air chambers;
wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;
wherein each of said first inclined air chambers is elongated in a second direction inclined relative to said first direction such that said longitudinal midline forms a downwardly opening acute angle with a central longitudinal line of each of said first inclined air chambers;
wherein each of said second inclined air chambers is elongated in a third direction inclined relative to said first direction such that said longitudinal midline forms a downwardly opening acute angle with a central longitudinal line of each of said second inclined air chambers;
wherein said air chambers further include a transverse air chamber elongated in said first direction and along said longitudinal midline, with said longitudinal midline being coincident with a central longitudinal line of said transverse air chamber; and
wherein said central longitudinal lines of said first inclined air chambers are inclined downwardly and outwardly from said central longitudinal line of said transverse air chamber in a direction toward said first longitudinal end of said air bladder, and said central longitudinal lines of said second inclined air chambers are inclined downwardly and outwardly from said central longitudinal line of said transverse air chamber in a direction toward said second longitudinal end of said air bladder, such that a first gap between said transverse air chamber and an innermost one of said first inclined air chambers is greater adjacent a bottom end of said transverse air chamber than adjacent a top end thereof, and such that a second gap between said transverse air chamber and an innermost one of said second inclined air chambers is greater adjacent said bottom end of said transverse air chamber than adjacent said top end thereof.

11. A therapeutic appliance as recited in claim 10, wherein said air chambers further include a first gap air chamber disposed in a lower end of said first gap, and a second gap air chamber disposed in a lower end of said second gap, said first and second gap air chambers being shorter in length than said transverse air chamber and said innermost ones of said first and second inclined air chambers.

12. A therapeutic appliance as recited in claim 11, wherein each of said first and second gap air chambers is substantially triangular in shape.

13. A therapeutic appliance for application to the sacrolumbar region of the human body to overlie the sacrum and sacroiliac joints, said appliance comprising:

an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said second inclined air chambers is elongated in a third direction inclined relative to said first direction such that said longitudinal midline forms a downwardly opening acute angle with a central longitudinal line of each of said second inclined air chambers; and wherein said central longitudinal lines of said first inclined air chambers are inclined downwardly and outwardly from said longitudinal midline in a direction toward said first longitudinal end of said air bladder, and said central longitudinal lines of said second inclined air chambers are inclined downwardly and outwardly from said longitudinal midline in a direction toward said second longitudinal end of said air bladder, such that a gap between an innermost one of said first inclined air chambers and an innermost one of said second inclined air chambers is greater between bottom ends of said innermost ones of said first and second inclined air chambers than between top ends thereof.

14. A therapeutic appliance as recited in claim 13, wherein said air chambers further include at least one gap air chamber disposed in a lower end of said gap, said at least one gap air chamber being shorter in length than said innermost ones of said first and second inclined air chambers.

15. A therapeutic appliance for application to the sacrolumbar region of the human body to overlie the sacrum and sacroiliac joints, said appliance comprising:

an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said second inclined air chambers is elongated in a third direction inclined relative to said first direction such that said longitudinal midline forms a downwardly opening acute angle with a central longitudinal line of each of said second inclined air chambers;

wherein said central longitudinal lines of said first inclined air chambers are inclined downwardly and outwardly, over entire lengths thereof, respectively, from said midline in a direction toward said first longitudinal end of said air bladder;

said central longitudinal lines of said second inclined air chambers are inclined downwardly and outwardly, over entire lengths thereof, respectively, from said midline in a direction toward said second longitudinal end of said air bladder;

wherein said first inclined air chambers are progressively shorter in length in a direction away from said longitudinal midline toward said first longitudinal end of said air bladder; and wherein said second inclined air chambers are progressively shorter in length in a direction away from said longitudinal midline toward said second longitudinal end of said air bladder.

16. A therapeutic appliance for application to the sacrolumbar region of the human body to overlie the sacrum and sacroiliac joints, said appliance comprising:

an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said second inclined air chambers is elongated in a third direction inclined relative to said first direction such that said longitudinal midline forms a downwardly opening acute angle with a central longitudinal line of each of said second inclined air chambers; and wherein said air chambers further include a plurality of first longitudinal air chambers elongated substantially in said longitudinal direction of said air bladder and disposed longitudinally between said first inclined air chambers and said first longitudinal end of said air bladder, and a plurality of second longitudinal air chambers elongated substantially in said longitudinal direction of said air bladder and disposed longitudinally between said second inclined air chambers and said second longitudinal end of said air bladder.

17. A therapeutic appliance for application to the sacrolumbar region of the human body to overlie the sacrum and sacroiliac joints, said appliance comprising:

an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said second inclined air chambers is elongated in a third direction inclined relative to said first direction such that said longitudinal midline forms a downwardly opening acute angle with a central longitudinal line of each of said second inclined air chambers; and wherein said air chambers constitute means for causing contraction of a longitudinal dimension of said air bladder upon inflation of said air chambers.

18. A therapeutic appliance for application to the sacrolumbar region of the human body to overlie the sacrum and sacroiliac joints, said appliance comprising:

an air bladder elongated along a longitudinal direction and having first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said second inclined air chambers is elongated in a third direction inclined relative to said first direction such that said longitudinal midline forms a downwardly opening acute angle with a central longitudinal line of each of said second inclined air chambers; and wherein said air chambers constitute means for causing contraction of said air bladder in directions downwardly and inwardly toward said longitudinal midline, upon inflation of said air chambers.

19. A therapeutic appliance for application to the sacrolumbar region of the human body to overlie the sacrum and sacroiliac joints, said appliance comprising:

an air bladder elongated along a longitudinal direction and having first and second longitudinal ends and top and bottom edges extending between said first and second longitudinal ends, said air bladder having a length in said longitudinal direction sufficient to wrap at least partly around the human body while overlying the sacrum and sacroiliac joints, said air bladder comprising a plurality of air chambers located between said first and second longitudinal ends;

at least one air supply passage coupled with at least one of said air chambers and in fluid communication with said plurality of said air chambers;

wherein said air chambers include a plurality of first inclined air chambers disposed longitudinally between said first longitudinal end of said air bladder and a longitudinal midline of said air bladder, and a plurality of second inclined air chambers disposed longitudinally between said second longitudinal end of said air bladder and said longitudinal midline of said air bladder, said longitudinal midline extending in a first direction transverse to said longitudinal direction of said air bladder and being disposed between said first and second longitudinal ends of said air bladder;

wherein each of said first inclined air chambers is elongated in a second direction inclined relative to said first direction such that said longitudinal midline forms a downwardly opening acute angle with a central longitudinal line of each of said first inclined air chambers;

wherein each of said second inclined air chambers is elongated in a third direction inclined relative to said first direction such that said longitudinal midline forms a downwardly opening acute angle with a central longitudinal line of each of said second inclined air chambers; and wherein said air bladder comprises a pair of sheets confronting one another, and said first and second inclined air chambers are defined by inclined seal lines formed by fused together portions of said sheets, each of said inclined seal lines extending continuously from a location adjacent said top edge of said air bladder to a location adjacent a bottom edge of said air bladder.

20. A therapeutic appliance as recited in claim 19, wherein said confronting sheets are further fused together along a longitudinally extending seal line extending adjacent said top edge of said air bladder; and said inclined seal lines join, at top ends thereof, with said longitudinally extending seal line.

21. A therapeutic appliance as recited in claim 19, wherein each of said inclined seal lines terminates in an enlarged strengthening seal portion.

* * * * *